United States Patent
Chung et al.

(10) Patent No.: US 9,187,767 B2
(45) Date of Patent: *Nov. 17, 2015

(54) METHOD FOR PRODUCING HYDROCARBONS FROM BIOMASS OR ORGANIC WASTE

(75) Inventors: Young Min Chung, Daejeon (KR); Cher Hee Park, Seoul (KR); Young Seek Yoon, Gwangju (KR); Hee Jung Jeon, Daejeon (KR); Hee Soo Kim, Daejeon (KR); Seung Hoon Oh, Seoul (KR); Seong Ho Lee, Seoul (KR); Ok Youn Kim, Daejeon (KR)

(73) Assignee: SK INNOVATION CO., LTD., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 13/879,904

(22) PCT Filed: Oct. 18, 2011

(86) PCT No.: PCT/KR2011/007748
§ 371 (c)(1),
(2), (4) Date: Apr. 17, 2013

(87) PCT Pub. No.: WO2012/053804
PCT Pub. Date: Apr. 26, 2012

(65) Prior Publication Data
US 2013/0210106 A1   Aug. 15, 2013

(30) Foreign Application Priority Data
Oct. 21, 2010   (KR) .......................... 10-2010-0103089

(51) Int. Cl.
| | | |
|---|---|---|
| *C12P 5/02* | (2006.01) | |
| *B01J 21/06* | (2006.01) | |
| *B01J 23/10* | (2006.01) | |
| *B01J 23/28* | (2006.01) | |
| *B01J 23/34* | (2006.01) | |
| *B01J 23/38* | (2006.01) | |
| *B01J 23/54* | (2006.01) | |
| *B01J 23/883* | (2006.01) | |
| *C07C 1/207* | (2006.01) | |
| *B01J 23/648* | (2006.01) | |
| *B01J 23/882* | (2006.01) | |
| *B01J 23/888* | (2006.01) | |

(52) U.S. Cl.
CPC ............. *C12P 5/026* (2013.01); *B01J 21/066* (2013.01); *B01J 23/10* (2013.01); *B01J 23/28* (2013.01); *B01J 23/34* (2013.01); *B01J 23/38* (2013.01); *B01J 23/6484* (2013.01); *B01J 23/882* (2013.01); *B01J 23/883* (2013.01); *B01J 23/888* (2013.01); *C07C 1/207* (2013.01); *C07C 2521/06* (2013.01); *C07C 2523/20* (2013.01); *C07C 2523/28* (2013.01); *C07C 2523/44* (2013.01); *C07C 2523/648* (2013.01); *C07C 2523/755* (2013.01); *C07C 2523/883* (2013.01)

(58) Field of Classification Search
None
See application file for complete search history.

(56) References Cited

U.S. PATENT DOCUMENTS

| 5,969,189 | A | 10/1999 | Holtzapple | |
|---|---|---|---|---|
| 2007/0135316 | A1* | 6/2007 | Koivusalmi et al. | 508/216 |
| 2007/0161832 | A1* | 7/2007 | Myllyoja et al. | 585/7 |
| 2008/0058563 | A1 | 3/2008 | Dumesic | |
| 2008/0071125 | A1* | 3/2008 | Li | 585/361 |
| 2009/0014354 | A1* | 1/2009 | Knuuttila et al. | 208/58 |
| 2009/0255171 | A1* | 10/2009 | Dumesic et al. | 44/308 |
| 2011/0152593 | A1* | 6/2011 | Kelly et al. | 585/319 |
| 2013/0017590 | A1 | 1/2013 | Chung | |

FOREIGN PATENT DOCUMENTS

| CN | 101326266 A | 12/2008 |
|---|---|---|
| JP | 4272345 B2 | 3/2009 |
| JP | 2009-518530 | 5/2009 |
| JP | 2009-530335 | 8/2009 |
| JP | 2010-202549 | 9/2010 |
| JP | 2010202549 A | 9/2010 |
| KR | 1020120009689 A | 2/2012 |
| WO | 9900512 | 1/1999 |
| WO | 2007068795 A1 | 6/2007 |
| WO | 2007107337 A1 | 9/2007 |
| WO | 2011115394 A2 | 9/2011 |

OTHER PUBLICATIONS

Pressure Unit Conversion. Datasheet [online].Avameg, Inc. Copyright 2013. [retrieved on Oct. 11, 2013]. Retrieved from the Internet: <URL: http://www.unit-conversion.info/pressure.html>. specif. p. 2.*
Advameg, Inc. Pressure Unit Conversion. Datasheet [online] Advameg, Inc. Copyright 2014. [retrieved on May 12, 2014]. Retrieved from the Internet: URL: < http://www.unit-conversion.info/pressure.htm> p. 1.*
Advameg, Inc. Pressure Unit Conversion.2. Datasheet [online] Advameg, Inc. Copyright 2014. [retrieved on May 12, 2014]. Retrieved from the Internet: URL: < http://www.unit-conversion.info/pressure.htm#data> p. 1.*
Online Conversion. Temperature Conversion. Datasheet [online]. Copyright 1997-2010 Robert Fogt. [retrieved on May 12, 2014]. Retrieved from the Internet: URL: <http://www.onlineconversion.com/temperature.htm> p. 1.*

(Continued)

*Primary Examiner* — John S Brusca
*Assistant Examiner* — Sharon M Papciak
(74) *Attorney, Agent, or Firm* — Abelman, Frayne & Schwab

(57) ABSTRACT

The present invention relates to a method for producing hydrocarbons from biomass or organic waste. The present invention provides: a method for effectively producing diverse hydrocarbons by using a raw material comprising mixed organic acids that can be obtained by anaerobic fermentation which is a fermentation process in biogasification technology; and a method for producing diverse products such as fuel, lube base oil and aromatics by using a raw material comprising mixed organic acids.

8 Claims, 1 Drawing Sheet

(56) References Cited

OTHER PUBLICATIONS

Hall, J.D. Lubricant Base Oils. In: Significance of Tests for Petroleum Products, 8th edition. Copyright 2010 ASTM International. Ed.: Salvatore J. Rand. West Conshohocken, PA. pp. 189-196. specif. pp. 189, 192.*

Kunkes, E.L. et al. 2008. Catalytic conversion of biomass to monofunctional hydrocarbons and targeted liquid-fuel classes. Science. Oct. 17 vol. 322: 417-421. specif. pp. 417, 420, 421.*

Osamu Nagashima et al., "Ketonization of carboxylic acids over CeO2-based composite oxides," Journal of Molecular Catalysis, 227:231-239 (2005).

International Search Report for PCT/KR2011/007748 dated Apr. 24, 2012 (6 pages).

Office Action, CN 2011800509798 (2 pages), and English Language Summary (2 pages).

Office Action, JP 2013-534811 dated Apr. 14, 2015), and English Language Summary (4 pages).

* cited by examiner

US 9,187,767 B2

METHOD FOR PRODUCING HYDROCARBONS FROM BIOMASS OR ORGANIC WASTE

RELATED APPLICATIONS

This application is a United States national phase application under 35 USC §371 of PCT/KR2011/007748 filed on Oct. 18, 2011, and claims the benefit under 35 USC §119 of Korean patent application number KR 10-2010-0103089 filed Oct. 21, 2010, the disclosures of which are incorporated herein by reference in their entireties.

TECHNICAL FIELD

The present invention relates to a method of efficiently producing diverse hydrocarbons from an organic acid mixture obtainable via anaerobic fermentation which is a fermentation process in biogasification technology and, more particularly to a method of producing a variety of products such as fuel, lube base oil, aromatics, etc., from an organic acid mixture.

BACKGROUND ART

Although chemical industries based on petroleum have been remarkably developed from the mid-20$^{th}$ century onwards, prices of petroleum, gas and coal, which are typical examples of fossil fuel, are continuously increasing due to limitations of the resources thereof, and competition among countries has intensified in order to efficiently secure them. Also, chemical products produced from fossil fuel generate large amounts of byproducts in the manufacturing process, such as waste and gases that contribute to global warming, undesirably contributing to a serious environmental crisis that may affect all mankind, and rapidly shrinking conventional chemical industries. Thus, it is required to develop novel eco-friendly biochemical processes using biomass, which may be applied instead of chemical processes based on fossil fuel.

Biomass commonly refers to a vegetable source such as corn, bean, flaxseed, rapeseed, sugarcane, and palm oil, but typically may include living organics, or metabolic byproducts of materials constituting any one part of a carbon cycle.

However, existing biomass conversion techniques are limited in terms of competition with conventional chemical/petroleum products based on crude oil, due to restrictions of feeds/location conditions, low yields, high production costs, limits of the product spectrum, etc.

Also, anaerobic fermentation is easily carried out, exhibits high yield, and enables treatment of a wide range of biomass and organic waste, including land-sea biomass such as wood, seaweeds, etc., agricultural waste such as food waste, sewage sludge, corn stalks, millet stalks, animal excretions, etc., and palm waste, but there are no high-value raising methods other than biogases.

Furthermore, research into production of alcohols or fuel hydrocarbons from an organic acid mixture obtained via anaerobic fermentation is ongoing recently, but such processes are complicated and various products cannot be selectively produced.

DISCLOSURE

Technical Problem

Accordingly, the present inventors have discovered that diverse hydrocarbons may be efficiently produced from an organic acid mixture obtainable via anaerobic fermentation which is a fermentation process in biogasification technology, and also, a variety of products such as fuel, lube base oil, aromatics, etc., may be produced from an organic acid mixture, and thus the present invention has been devised to meet the demand of markets with regard to the above technical processes.

Therefore, an object of the present invention is to provide a novel method of producing diverse hydrocarbons from an organic acid mixture while efficiently saving energy.

Technical Solution

In order to accomplish the above object, the present invention provides a method of producing a hydrocarbon from biomass or organic waste, comprising (a) subjecting the biomass or organic waste to anaerobic fermentation, thus preparing an organic acid mixture; (b) subjecting the organic acid mixture to ketonization using a catalyst, thus preparing a ketone mixture; and (c) converting the ketone mixture into the hydrocarbon using a catalyst by means of a single reactor, wherein (b) and (c) are performed in the presence of water.

Advantageous Effects

According to the present invention, an innovative method is provided, which enables the production of desired products in a one-pot reaction via novel catalytic technology using various kinds of feeds including biomass or organic waste, thereby changing the paradigm of production techniques of chemical/petroleum products which enable global expansion adapted to feeds, location conditions, and targets-products.

In particular, diverse hydrocarbons can be selectively produced from an organic acid mixture, and energy can be efficiently saved in a one-pot reaction, thereby maximizing value addition of final products.

BEST MODE

Hereinafter, a detailed description will be given of the present invention.

The present invention pertains to a method of producing hydrocarbons from biomass or organic waste. According to the present invention, biomass or organic waste used as a feed may be selected from the group consisting of corn stalks, palm waste, food waste, sludge and mixtures thereof, but is not limited thereto.

Meanwhile, a fermentation process in typical biogasification technology includes two anaerobic fermentations, wherein an organic acid mixture is obtained via the first anaerobic fermentation, and biogas is produced via the second anaerobic fermentation.

The present invention is intended to provide a method of efficiently producing diverse hydrocarbons from an organic acid mixture obtainable via the first anaerobic fermentation in biogasification technology. According to the present invention, various kinds of products such as fuel, lube base oil, aromatics, etc, may be selectively produced from the organic acid mixture obtained via the anaerobic fermentation.

Figure 1:
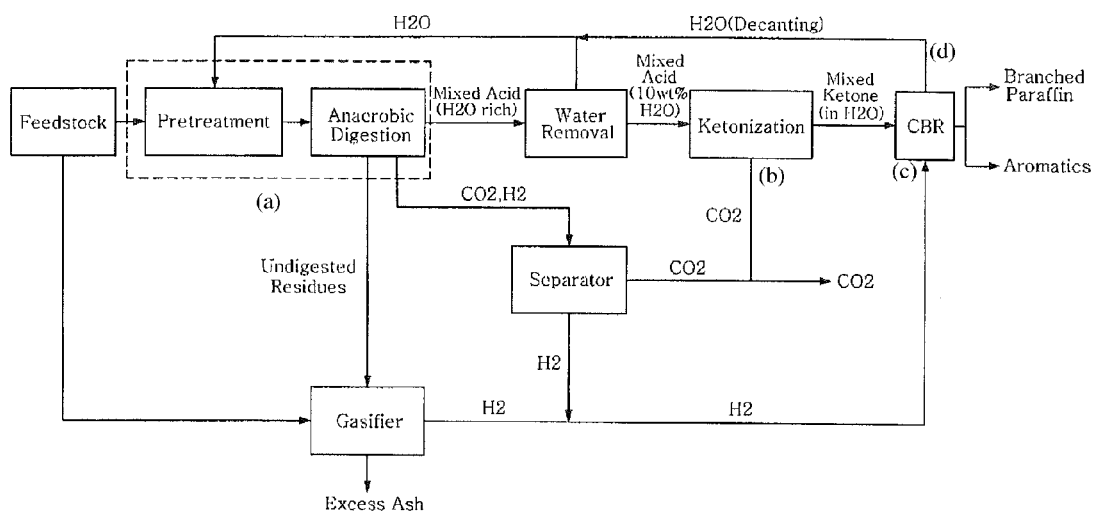
FIG. 1 illustrates a schematic flow of anaerobic fermentation in the presence of a solid material according to the present invention.
Figure 2:
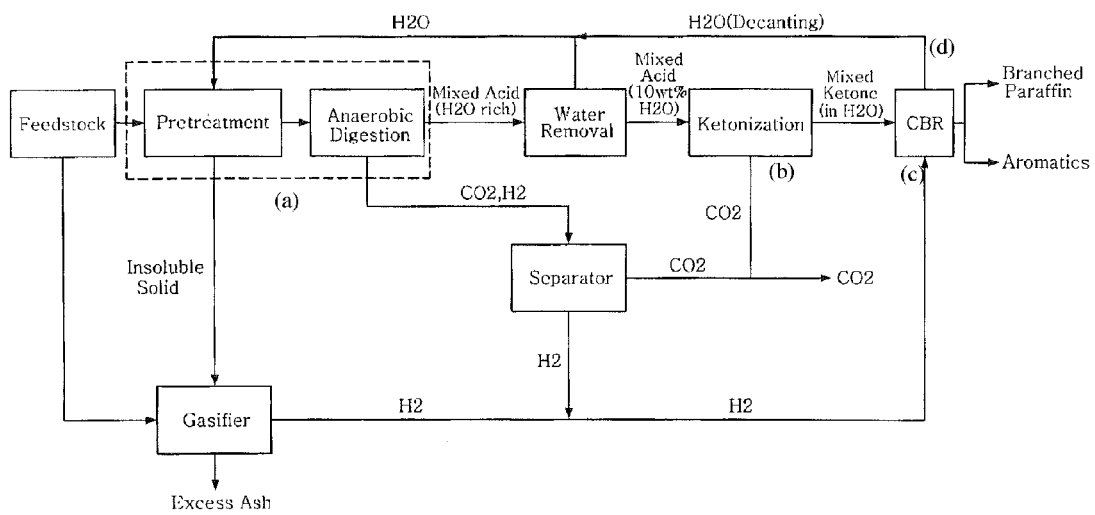
FIG. 2 illustrates a schematic flow of anaerobic fermentation in the absence of the solid material according to the present invention.

The schematic flow of the method according to the present invention is illustrated in FIGS. 1 and 2. With reference to FIGS. 1 and 2, the method of the invention includes (a) subjecting biomass or organic waste to anaerobic fermentation, thus preparing an organic acid mixture; (b) subjecting the organic acid mixture to ketonization using a catalyst, thus preparing a ketone mixture; and (c) converting the ketone mixture into a hydrocarbon using a catalyst by means of a single reactor, wherein (b) and (c) are performed in the presence of water.

FIGS. 1 and 2 illustrate the schematic flow of the anaerobic fermentation, in which the biomass or organic waste useful as a feed is introduced into a reactor, so that it is converted into an organic acid mixture via the anaerobic fermentation. In conventional cases, because water should be thoroughly removed to achieve thermal decomposition of an organic acid salt mixture, energy is required in a considerably large amount. However, in the above procedure, the preparation of the organic acid salt mixture is omitted, and thus ketonization is carried out using the catalyst in the presence of a predetermined amount of water.

Subsequently, the ketone mixture obtained via ketonization is converted into the hydrocarbon using the catalyst. In conventional cases, the reaction is carried out using a ketone mixture alone by removing water from a blend of water and ketone mixture obtained via the ketonization. However, in the above procedure, the blend of water and ketone mixture may be used as it is, thus saving energy necessary for removing water.

In the schematic flows of FIGS. 1 and 2, CBR (catalytic biomass refinery) is the conversion of the ketone mixture into the hydrocarbon, wherein a ketone mixture obtained via various methods is reacted in such a manner that aldol condensation, hydrogeneation, and hydrodeoxygenation are performed alone or sequentially using a single reactor in the presence of a catalyst, thus producing the hydrocarbon at high yield.

In (a), the biomass or organic waste is subjected to anaerobic fermentation, thus preparing the organic acid mixture. To this end, a feed material subjected to pretreatment such as crushing, etc. is blended with water and the resulting blend is placed in an acid fermentation bath containing fermentation strains, after which anaerobic fermentation is carried out at a predetermined reaction temperature for a predetermined period of time. Thereby, the organic acid mixture dissolved in water may be obtained.

Also, to prepare ketone from the organic acid mixture in (b), organic acids should be primarily recovered from water. As such, because typical separation methods make it difficult to separate the organic acids and water, in which an azeotropic phenomenon occurs, the ketone is typically prepared in such a manner that a salt is added during or after the fermentation process to form an organic acid salt mixture, which is then thermally decomposed to produce the ketone. In this case, complicated preparation and recovery of the organic acid salt mixture are essential, and also, water should be thoroughly removed to thermally decompose the organic acid salt mixture, and thus a large amount of energy is required, and the thermal decomposition of the organic acid salt also needs a large amount of energy. However, according to the present invention, the case where ketone is prepared via ketonziation using the catalyst obviates the complicated preparation and recovery of the organic acid salt mixture and may substitute for the thermal decomposition process which requires a large amount of energy. Furthermore, because the ketonization enables the catalytic reaction to take place even in the presence of a predetermined amount of water, when high ketone yield may be attained using a catalyst having water resistance, energy necessary for removing water may be additionally saved.

When (b) is carried out at 150~400° C. and a pressure of 1~50 atm, high yield may be obtained in terms of preventing the decomposition of acid mixture, in addition to high catalytic activity. Particularly, (b) may be performed at 200~300° C. and a pressure of 5~30 atm.

Moreover, (b) is performed using the catalyst, and the catalyst includes a material selected from the group consisting of MnO, (CeO$_2$), (ZnO$_2$), CaO, MgO, ZrO, BeO, SrO, BaO, K$_2$O, Rb$_2$O, Cs$_2$O, Na$_2$O, Li$_2$O and oxide mixtures thereof.

To prepare the hydrocarbon from the ketone mixture obtained in (b), in conventional cases, the reaction is carried out using the ketone mixture alone by removing water from the blend of water and ketone mixture obtained via the ketonization. However, in the present invention, the blend of water and ketone mixture obtained via the ketonization may be used as it is, and hydrocarbon and water may undergo phase separation after the reaction, thus easily separating the product from water and saving energy necessary for removing water.

In (c), the reaction is preferably carried out using a single catalyst system, and the single catalyst system may be formed via physical mixing, molding using a binder material, or formation of a double layer of catalysts.

Specifically, the catalyst used in (c) may include a material selected from the group consisting of CeZrO$_x$, CuZrO$_x$ (O$_x$ is an oxide), hydrotalcite, niobium oxide, alumina, silica, silica-alumina, zirconia, titania, oxide mixtures thereof, molecular sieves including zeolite, Pd, Pt, Rh, Ru, Ni, NiMo, CoMo, NiW, and CoW. The single catalyst system in (c) is specifically disclosed in Korean Patent Application No. 10-2010-0069983, which is incorporated in the present invention.

(c) may be performed at 80~500° C. in the hydrogen pressure range of 1~200 bar, and preferably at 100~400° C. in the hydrogen pressure range of 5~50 bar. Furthermore, WHSV in the single reactor is adjusted to 1/hr or less but exceeding zero, and preferably to 0.6/hr or less but exceeding zero. Also, the hydrocarbon prepared in (c) is any one selected from among fuel, lube base oil, and aromatics.

In the case of hydrogen necessary for the reaction, feeding an unreacted solid residue into a gasifier upon preparation of the organic acid mixture may be utilized in H$_2$ production, and directly feeding a part of the feed into the gasifier before fermentation may also be utilized in H$_2$ production.

In the present invention, various kinds of feed mixtures, including wood, seaweeds, organic waste, etc., may be used, and desired products may be produced in a one-pot reaction using novel catalytic technology, thus enabling global expansion adapted to feeds, location conditions, and targets-products. The effect caused by the one-pot reaction is more specifically shown in the following examples.

To additionally describe the principle of the invention, examples are described below. However, the present examples are not construed to limit the scope of the present invention considered by the present inventors.

EXAMPLE

Example 1

Ketonization

In the present example, a catalyst was prepared with reference to the known literature [J. Mol. Cat. A 227 (2005) 231].

Specifically, a catalyst was prepared in such a manner that a 10 wt % precursor aqueous solution comprising Ce(NO$_3$)$_3$·6H$_2$O (40 mol %) and Mn(NO$_3$)$_3$·6H$_2$O (60 mol %) was prepared, and then co-precipitated while being dropped into 200 ml of a 5M ammonia aqueous solution with vigorous stirring. The precipitated catalyst was washed three times with distilled water and then dried at 1100° C. for 24 hr. Subsequently, burning at 550° C. for 2 hr was performed, thus obtaining a catalyst 5 g of the CeO$_2$—Mn$_2$O$_3$ catalyst thus prepared was placed in a continuous reactor and then pretreated at 400° C. for 1 hr under atmospheric pressure using N$_2$ (400 cc/min). After the pretreatment, the temperature of the reactor was decreased to 350° C., and a feed comprising 70 wt % of acetic acid, 10 wt % of propionic acid, 10 wt % of butyric acid, and 10 wt % of H$_2$O was fed into a reactor at 3 cc/min so that the reaction could be carried out. During the reaction, the flow rate of N$_2$ was maintained at 400 cc/min. The organic composition of the sample obtained after the reaction was analyzed via GC and GC-MS. The composition of the sample obtained after 24 hr of the reaction is shown in Table 1 below. The amount of water was analyzed to be 25.3 wt % using a Karl-Fischer method.

TABLE 1

| Composition | Amount (mol %) |
|---|---|
| Acetic acid | 0.7 |
| Propionic acid | 0.7 |
| Butyric acid | 1.6 |
| Dimethyl ketone | 77.6 |
| Methyl ethyl ketone | 9.5 |
| Methyl propyl ketone | 3.7 |
| Diethyl ketone | 1.6 |
| Ethyl propyl ketone | 0.3 |
| Dipropyl ketone | 0.1 |
| Others | 4.1 |

Example 2

Preparation of Hydrocarbon

A hydrocarbon was prepared from a ketone mixture aqueous solution comprising 60 wt % of dimethyl ketone (acetone), 10 wt % of methyl ethyl ketone, and 30 wt % of H$_2$O using a catalyst system comprising 0.25 wt % Pd/Nb$_2$O$_5$ and Ni—Mo/ZrO$_2$ mixed together. The 0.25 wt % Pd/Nb$_2$O$_5$ catalyst was prepared by immersing Pd(NO$_3$)$_2$ (10 wt % Aldrich) in niobic acid using an incipient wetness method, and performing drying at 393 K for 3 hr and burning at 533 K for 3 hr in an air atmosphere. The Ni—Mo/ZrO$_2$ catalyst was prepared by supporting about 10 wt % of Mo and about 3 wt % of Ni on ZrO$_2$. As such, the Mo precursor used therefor was ammonium heptamolybdate tetrahydrate (AHM), and the Ni precursor was nickel nitrate hexahydrate (NNH). Specifically, an aqueous solution obtained by dissolving AHM in distilled water was supported on ZrO$_2$, dried at 423 K for 2 hr, and continuously burned at 732 K for 2 hr, thus preparing Mo/ZrO$_2$. Subsequently, NNH was dissolved in distilled water, after which the Mo/ZrO$_2$ catalyst was supported, dried at 423 K for 2 hr, and then continuously burned at 732 K for 2 hr, thus preparing the Ni—Mo/ZrO$_2$ catalyst.

The reaction was performed using a high-pressure microreactor, and 3 g each, that is, a total of 6 g, of the two catalysts thus prepared was mixed physically, thus preparing the catalyst which was then used to perform the reaction. The reduction of the catalyst was conducted by increasing the temperature to 723 K at a rate of 0.5° C./min, maintaining the increased temperature for 2 hr, and then decreasing the temperature to 623 K, under the flow of hydrogen at 200 ml/min. At 623 K, the ketone mixture was introduced at WHSV of 0.5 h$^{-1}$, and hydrogen was adjusted to 50 bar. The sample obtained after the reaction underwent phase separation into an organic phase and a water phase, and the conversion of the reactant and the selectivity of the product were determined by analyzing the organic phase using GC-Mass. The results are given in Table 2 below. An insignificant amount of acetone was detected in the water phase.

TABLE 2

| Composition | Amount (mol %) |
|---|---|
| Dimethyl ketone | 0.1 |
| Methyl ethyl ketone | 0.2 |
| Branched ketone (C$_5$~C$_{12}$) | 1.2 |
| Paraffin (C$_3$~C$_{12}$) | 90.1 |
| Olefin | 0.1 |
| Aromatics | 5.5 |
| Alcohol | 0.1 |
| Known | 2.7 |

Although the embodiments of the present invention have been disclosed for illustrative purposes, those skilled in the art will appreciate that a variety of different modifications and variations are possible, without departing from the scope and spirit of the invention. Accordingly, such modifications and variations should also be understood as falling within the claims of the present invention.

The invention claimed is:

1. A method of producing hydrocarbons, comprising:
   (a) subjecting biomass or organic waste to anaerobic fermentation to prepare an aqueous organic acid mixture;
   (b) subjecting the aqueous organic acid mixture to ketonization using a catalyst to prepare an aqueous ketone mixture;
   (c) subjecting the aqueous ketone mixture to aldol condensation and hydrogenation/hydrodeoxygenation to convert the ketone mixture into the hydrocarbons in the presence of combined catalysts comprising a catalyst having consisting of an aldol condensation catalyst and a hydrogenation/hydrodeoxygenation catalyst under a hydrogen atmosphere in a single reactor, the hydrocarbons selected from the group consisting of fuel, lube base oil, and aromatics; and
   (d) separating the resulting mixture of hydrocarbons and water obtained in step (c) into the hydrocarbons as an organic phase and the water as an aqueous phase via phase separation, followed by recovering the hydrocarbons,
   wherein steps (b) and (c), respectively, are performed in presence of water,
   wherein the aqueous ketone mixture of step (b) is used as it is without removing water therefrom in step (c),
   wherein the aldol condensation catalyst is selected from the group consisting of CeZrO$_x$, CuZrO$_x$, niobium oxide, zirconia, titania, and oxide mixtures thereof,
   wherein the hydrogenation/hydrodeoxygenation catalyst is selected from the group consisting of Pd, Pt, Rh, Ru, Ni, NiMo, CoMo, NiW, CoW, and mixtures thereof;
   wherein the catalyst used in step (b) includes a material selected from the group consisting of MnO, CeO$_2$, ZnO, CaO, MgO, ZrO$_2$, BeO, SrO, BaO, K$_2$O, Rb$_2$O, Cs$_2$O, Na$_2$O, Li$_2$O, and oxide mixtures thereof, and
   wherein step (c) is performed in the presence of a single catalyst system having the aldol condensation catalyst and the hydrogenation/hydrodeoxygenation catalyst, formed by physical mixing, molding using a binder material or double layering.

2. The method of claim 1, wherein step (b) is performed at 150-400° C. and a pressure of 1-50 atm.

3. The method of claim 2, wherein step (b) is performed at 200-300° C. and a pressure of 5-30 atm.

4. The method of claim 1, wherein the aldol condensation and hydrogenation/hydrodeoxygenation in step (c) is performed at 80-500° C. in a hydrogen pressure range of 1-200 bar.

5. The method of claim 4, wherein the aldol condensation and hydrogenation/hydrodeoxygenation in step (c) is performed at 100-400° C. in a hydrogen pressure range of 5-50 bar.

6. The method of claim 4, wherein weight hourly space velocity (WHSV) in the single reactor is adjusted to 1/hr or less.

7. The method of claim 1, further comprising: feeding a solid residue of the biomass or the organic waste generated from step (a) to a gasifier to produce hydrogen, and utilizing the produced hydrogen for step (c).

8. The method of claim 1, wherein hydrocarbons produced in step (c) comprise fuel, lube base oil and aromatics.

\* \* \* \* \*